US006165167A

United States Patent [19]
Delaloye

[11] Patent Number: 6,165,167
[45] Date of Patent: Dec. 26, 2000

[54] RAPID EXCHANGE CATHETER SYSTEM

[75] Inventor: Stéphane Delaloye, Bulach, Switzerland

[73] Assignee: Schneider (Europe) GmbH, Switzerland

[21] Appl. No.: 08/990,174

[22] Filed: Dec. 15, 1997

[30] Foreign Application Priority Data

Jun. 10, 1997 [EP] European Pat. Off. ............. 97201746

[51] Int. Cl.$^7$ .............................................. A61M 25/098
[52] U.S. Cl. ...................... 604/528; 604/103.04; 604/523
[58] Field of Search ........................... 604/96.01, 103.04, 604/264, 523, 528; 606/191, 194

[56] References Cited

U.S. PATENT DOCUMENTS

| | | | |
|---|---|---|---|
| 4,573,470 | 3/1986 | Samson et al. ........................ | 128/344 |
| 4,616,648 | 10/1986 | Simpson ................................. | 128/303 |
| 4,655,746 | 4/1987 | Daniels et al. ........................... | 604/53 |
| 4,681,110 | 7/1987 | Wiktor .................................... | 128/343 |
| 4,732,152 | 3/1988 | Wallsten et al. ........................ | 128/343 |
| 4,733,665 | 3/1988 | Palmaz ................................... | 128/343 |
| 4,748,982 | 6/1988 | Horzewski et al. ..................... | 128/344 |
| 4,762,129 | 8/1988 | Bonzel .................................... | 128/344 |
| 4,771,777 | 9/1988 | Horzewski et al. ..................... | 128/344 |
| 4,793,348 | 12/1988 | Palmaz ................................... | 128/325 |
| 4,824,435 | 4/1989 | Giesy et al. .............................. | 604/49 |
| 4,848,343 | 7/1989 | Wallsten et al. ........................ | 128/343 |
| 4,877,031 | 10/1989 | Conway et al. ........................ | 128/344 |
| 4,966,148 | 10/1990 | Millar ..................................... | 128/637 |
| 4,988,356 | 1/1991 | Crittenden et al. ..................... | 606/192 |
| 5,002,531 | 3/1991 | Bonzel .................................... | 604/96 |
| 5,026,377 | 6/1991 | Burton et al. ........................... | 606/108 |
| 5,034,001 | 7/1991 | Garrison et al. ........................ | 604/53 |
| 5,040,548 | 8/1991 | Yock ....................................... | 128/898 |
| 5,061,273 | 10/1991 | Yock ....................................... | 606/194 |
| 5,102,403 | 4/1992 | Alt .......................................... | 604/280 |
| 5,135,535 | 8/1992 | Kramer ................................... | 606/194 |
| 5,180,368 | 1/1993 | Garrison ................................. | 604/104 |
| 5,201,757 | 4/1993 | Heyn et al. .............................. | 606/198 |
| 5,203,772 | 4/1993 | Hammerslag et al. .................. | 604/95 |
| 5,232,445 | 8/1993 | Bonzel et al. ........................... | 604/96 |
| 5,290,295 | 3/1994 | Querals et al. .......................... | 606/108 |
| 5,337,733 | 8/1994 | Bauerfeind et al. ..................... | 128/4 |
| 5,364,376 | 11/1994 | Horzewski et al. ..................... | 604/280 |
| 5,458,605 | 10/1995 | Klemm ................................... | 606/108 |
| 5,458,613 | 10/1995 | Gharibadeh et al. .................... | 606/194 |
| 5,458,615 | 10/1995 | Klemm et al. .......................... | 606/198 |
| 5,484,444 | 1/1996 | Braunschweiler et al. ............. | 606/108 |
| 5,484,449 | 1/1996 | Amundson et al. ..................... | 606/108 |
| 5,507,768 | 4/1996 | Lau et al. ................................ | 606/198 |
| 5,656,013 | 8/1997 | Yoon ...................................... | 600/207 |
| 5,690,644 | 11/1997 | Yurek et al. ............................ | 606/108 |
| 5,823,995 | 10/1998 | Fitzmaurice et al. ................... | 604/96 |
| B1 4,655,771 | 9/1996 | Wallsten ................................. | 623/1 |
| B1 4,762,129 | 7/1991 | Bonzel .................................... | 606/194 |

FOREIGN PATENT DOCUMENTS

| | | |
|---|---|---|
| 0321912A1 | 6/1989 | European Pat. Off. . |
| 0416662A2 | 3/1991 | European Pat. Off. . |
| 0442657A2 | 8/1991 | European Pat. Off. . |
| 0505686B1 | 9/1992 | European Pat. Off. . |
| 0513818A1 | 11/1992 | European Pat. Off. . |
| 3935256C1 | 1/1991 | Germany . |
| 9317636 | 3/1993 | WIPO . |
| 93177750 | 9/1993 | WIPO . |
| 94/15549 | 7/1994 | WIPO . |
| 95/32011 | 11/1995 | WIPO . |

*Primary Examiner*—Sharon Kennedy
*Assistant Examiner*—Cris L. Rodriguez
*Attorney, Agent, or Firm*—Todd P. Messal

[57] ABSTRACT

In a catheter system for rapid exchange via a guidewire with a flexible, elongated inner catheter, which has a proximal end and a distal end as well as a guidewire lumen, which extends from an insertion port on the distal end to a lateral through port distally from the proximal end, and a flexible, tubular outer catheter, in which the inner catheter is disposed axially displaceably, and which has a lateral exit port for the guidewire, retaining means are provided on the inner catheter and the outer catheter, which retaining means prevent twisting of the outer catheter relative to the inner catheter. Thus, the through port and the exit port remain aligned with each other and the catheter system can be displaced simply along the guidewire. In addition, the outer catheter can be readily displaced relative to the inner catheter.

7 Claims, 1 Drawing Sheet

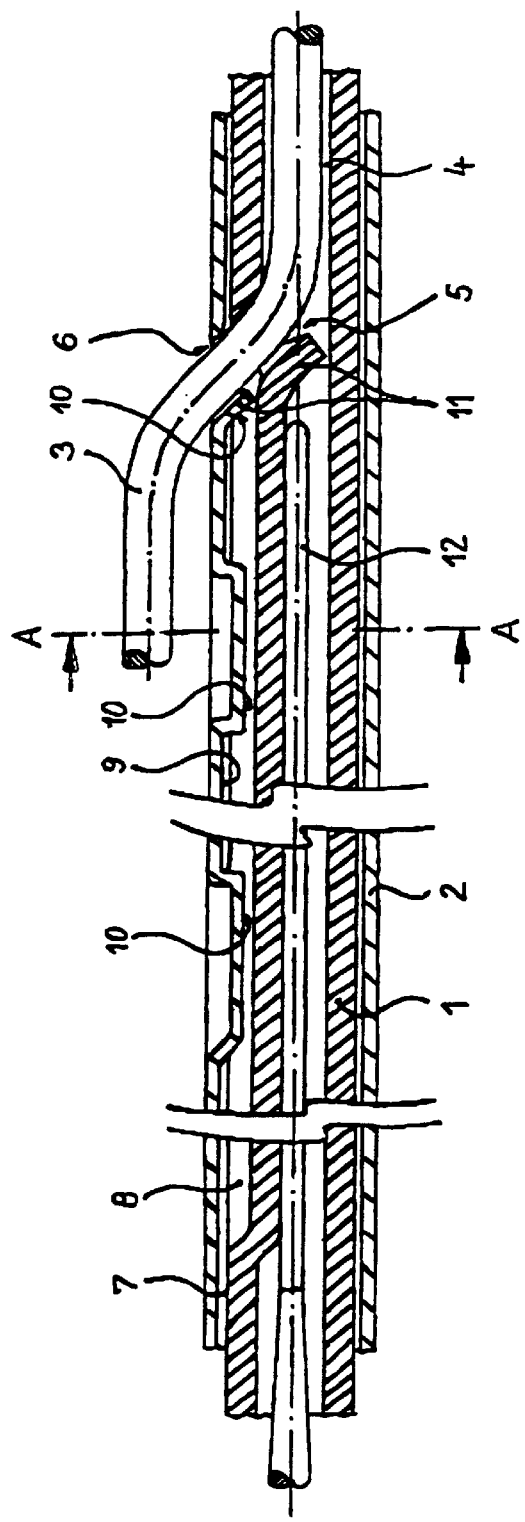
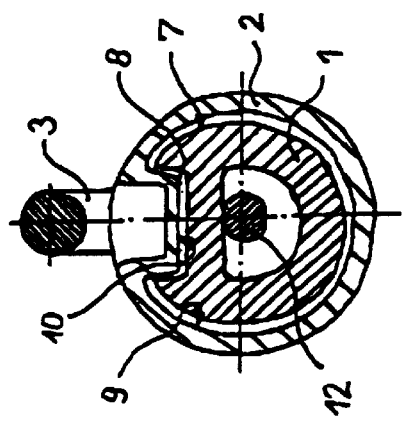

RAPID EXCHANGE CATHETER SYSTEM

BACKGROUND OF THE INVENTION

This application claims priority under 35 U.S.C. § 119 of European Patent Application No. 97201746.1, filed in the European Patent Office on Jun. 10, 1997.

The invention relates to a catheter system for rapid exchange via a guidewire with a flexible, elongated inner catheter, which has a proximal end and a distal end as well as a guidewire lumen, which extends from an insertion port on the distal end to a lateral through port distally from the proximal end, and a flexible, tubular outer catheter, inside which the inner catheter is disposed axially displaceably and which has a lateral exit port for the guidewire.

Catheter systems with two catheters disposed one inside the other and displaceable relative to each other have many potential uses in interventions in body cavities, such as in blood vessels, air passages, or the esophagus. Usually, the catheter system is inserted along a pre-positioned guidewire through a body lumen to the desired site for use there.

For example, U.S. Pat. No. 4,655,746 discloses a catheter system, in which the inner and outer catheters are designed as balloon catheters, such that a vascular segment bounded by the balloons may be sealed relative to the rest of the vascular system. The distance between the balloons and thus the length of the vascular segment to be sealed may be adjusted by shifting the outer catheter relative to the inner catheter. Via a lumen provided for this, a therapeutic substance is infused into the sealed vascular segment or fluid is aspirated therefrom. The guidewire lumen extends in this catheter system over the entire length of the inner catheter. A catheter exchange with an indwelling guidewire requires either a very long guidewire or the attachment of an extension. Either is very time-consuming and represents an additional strain on the patient. Moreover, a second person must assist during such an intervention, and a large area around the puncture opening must be kept sterile.

To overcome the aforementioned disadvantages, catheter systems have been developed in which the guidewire lumen extends over only a short distal portion, and the guidewire runs for most of its length beside the catheter system to the proximal end. The guidewire protrudes out of the body by only roughly the length of the guidewire lumen, whereby a rapid catheter exchange is possible without attachment of an extension.

From EP 0 505 686 B1, a catheter system of the type mentioned in the introduction is known, in which the inner catheter is designed as a rapidly exchangeable balloon catheter with a premounted stent, whereas the outer catheter serves as a protective sheath during insertion of the stent. The guidewire leaves the catheter system proximally through two mutually aligned ports in the inner and outer catheters. To insert the catheter system, the two ports are at least partially aligned such that the catheter system can move along the guide wide. To expand the stent, the outer catheter is retracted along the inner catheter, whereby the guidewire ports move against each other and the guidewire runs between the openings in an annular lumen between the inner and outer catheter. After successful stent implantation, the outer catheter, which has a slot for this purpose extending from the guidewire port to the distal end of the outer catheter, may first be retracted. Then, the balloon catheter is removed from the body in a known manner along the guidewire. In the manipulation of such a catheter system in the vascular system of a patient, for example, it is possible for the inner and outer catheters to twist against each other, particularly in the distal portion of the catheter system, whereby the mutual position of the guidewire ports changes. During insertion or withdrawal of the catheter system, this results in undesired clamping of the guidewire in the zone of the ports, which significantly hinders rapid and uniform movement of such a catheter system. In addition, the guidewire ports may lose their mutual alignment during displacement of the outer catheter along the inner catheter, and additional frictional forces between the guidewire and the rim of the port may have to be overcome. And finally, during retraction of the outer catheter, the guidewire may be pressed into the slot and become clamped there.

WO 94/15549 discloses a likewise rapidly exchangeable catheter system. A self-expanding stent, which is confined in its compressed state between an inner and an outer catheter on the distal end of the catheter system, is released by retracting the outer catheter relative to the inner catheter. The guidewire leaves the catheter system proximally through a lateral port in the inner catheter and a slot in the outer catheter. An elongated depression, in which the guidewire can lie during retraction of the outer catheter, connects proximally to the port in the inner catheter. Thus, the guidewire is gently guided out of the catheter system without sharp bending. The slot in the outer catheter is, however, so narrow that significant frictional forces occur during displacement of the catheter system along the guidewire, and also during retraction of the outer catheter. Moreover, the catheter system suffers from the disadvantage that the slot and the depression reduce the cross-section and thus the kink resistance of the catheter system, in particular when the slot and the depression extend to the proximal end of the catheter system.

All documents cited herein, including the foregoing, are incorporated herein by reference in their entireties for all purposes.

SUMMARY OF THE INVENTION

Consequently, the object of the invention is a catheter system which is evenly and easily movable along a guidewire and whereby the outer catheter can be retracted simply relative to the inner catheter.

The object is accomplished according to the present invention. If retaining means, which prevent twisting of the outer catheter relative to the inner catheter, are provided on the inner catheter and the outer catheter, whereby the through port and the exit port remain aligned with each other, the guidewire is provided with a large port area to leave the catheter system. Clamping of the guidewire between the through port and the exit port is thus avoided both during advancing or retraction of the entire catheter system along the guidewire and during displacement of the outer catheter relative to the inner catheter. A catheter system according to the invention thus has improved sliding properties, which facilitate its manipulability in practical use.

In an advantageous embodiment of the invention, the retaining means are formed interlockingly by a depression in the outer wall of the inner catheter and by at least one protrusion on the inner wall of the outer catheter which engages in the depression. Thus, a simple to manufacture twist protection between the inner catheter and the outer catheter is provided, which does not impair axial displacement of the outer and the inner catheter relative to each other. The retaining means are integrated into the catheter system such that it is unnecessary to carry out any enlargement of the profile. Without leaving the scope of patent protection, the depression may alternatively also be made in the outer catheter and the protrusions on the inner catheter; even a hybrid form is conceivable.

In a preferred embodiment of the invention, the depression has an elongated shape with axial alignment. The protection against twisting here also satisfies the additional object of guiding the outer shaft during retraction relative to the inner shaft. In addition, with this measure it is also possible to define a distal and proximal end position of the outer shaft relative to the inner shaft.

The protrusion is, in its axial dimension, preferably small in comparison to the length of the depression. Thus, the length of the depression may remain as small as possible, i.e., roughly in the size range indicated by practical application—i.e., for example, the maximum length of a vascular segment to be sealed by two balloons or the length of the stent used. Moreover, the frictional area between the protrusion and the depression is reduced, which contributes to simple manipulation of a catheter system according to the invention during displacement of the outer catheter.

In an advantageous embodiment of the invention, the through port is disposed on the distal end of the depression. In this arrangement, the guidewire may lie in the depression during retraction of the outer catheter, whereby sharp bending of the guidewire as it leaves the catheter system is avoided. In addition, the guidewire does not take up any cross-sectional space inside the inner catheter in the region of the depression. Thus, the overall cross-section of the catheter system may be kept small.

In a preferred embodiment of the invention, the exit port passes through the protrusion. The protection against twisting and the guidance here are particularly efficient since they directly affect the course of the guidewire, by keeping the exit port and the through port aligned with each other in each catheter position. The design also has advantages in terms of production technology, since the exit port and protrusion can be produced with a single production process.

The through port and the exit port of a catheter system according to the invention are advantageously provided with guiding aids for the distal insertion of the guidewire. The guidewire threaded into the distal end of the catheter system is thus guided during advancement of the catheter system without additional manipulation through the through port and the exit port out of the guidewire lumen. A catheter system according to the invention may thus be inserted quickly and without problems via a pre-positioned guidewire.

BRIEF DESCRIPTION OF THE DRAWINGS

Additional advantages of a catheter system according to the invention are revealed through a preferred exemplary embodiment, which is explained in detail with reference to the drawings, in which:

FIG. 1 depicts a longitudinal section of the catheter system, and

FIG. 2 depicts a cross-section of the catheter system along the intersecting line A—A in FIG. 1.

DETAILED DESCRIPTION OF THE INVENTION

FIG. 1 and FIG. 2 depict a catheter system according to the invention with a flexible, elongated inner catheter 1 and a flexible, tubular outer catheter 2, which is suitable for rapid exchange via a guidewire 3. For this, the guidewire lumen 4 extends from the insertion port (not shown) on the distal end (not shown) of the inner catheter 1 to a through port 5, which is positioned distally relative to the proximal end (not shown) of the inner catheter 1. The outer catheter 2 has a lateral exit port 6 for the guidewire 3, from which the guidewire 3 runs in the proximal direction along with the catheter system.

The inner catheter 1 has on its outer wall 7 an elongated, axially aligned depression 8, in which protrusions 10 disposed on the inner wall 9 engage. This yields an interlocking protection against twisting between the inner catheter 1 and the outer catheter 2, which keeps the exit port 6 and the through port 5 aligned with each other both during displacement of the entire catheter system along the guidewire 3 and also during displacement of the outer catheter 2 relative to the inner catheter 1. Thus, the guidewire 3 is provided in all positions with as large an area as possible for its exit from the catheter system, and the friction between the guidewire 3 and the through port 5 or the exit port 6 is kept low. The manipulation of a catheter system according to the invention is made significantly easier since position-associated frictional resistances do not have to be overcome. For additional ease of manipulation, the through port 5 and the exit port 6 are provided with guide aids 11 which allow the guidewire 3 threaded through the insertion port into the guidewire lumen 4 from the distal end to find its way through the through port 5 and the exit port 6 without additional manipulations during the advancing of the catheter system.

The depression 8 and protrusion 10 may, for example, be stamped simply in the inner catheter 1 and outer catheter 2 by thermoforming by means of shaping tools. The guiding aids 11 may likewise be produced without additional expense during the incorporation of the through port 5 and the exit port 6, by forming them from the excess material on the edges of the bore.

In the inner catheter 1 runs a stiffening wire 12 tapering in the distal direction, which contributes to the support of the section in which the depression 8 is disposed.

The above-described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A catheter system for rapid exchange over a guide wire comprising:
    a flexible, elongated inner catheter having a proximal end, a distal end, a guide wire lumen, the guide wire lumen extending from an insertion port at the distal end of the inner catheter to a lateral through port; and
    a flexible, tubular outer catheter, disposed about the inner catheter and axially displaceable relative to the inner catheter, and having a lateral exit port for the guide wire aligned with the through port, wherein a retaining means is provided on the inner catheter and the outer catheter to prevent twisting of the outer catheter relative to the inner catheter so that the through port and the exit port remain aligned with one another.

2. The catheter system according to claim 1, wherein the retaining means comprises:
    a depression in the outer wall of the inner catheter; and
    at least one protrusion on the inner wall of the outer catheter, the depression in the outer wall of the inner catheter interlockingly engaging the protrusion on the inner wall of the outer catheter.

3. The catheter system of claim 2 wherein the depression is elongated with axial alignment.

4. The catheter system of claim 2 wherein the protrusion has an axial dimension and a length, the axail dimension smaller than the length of the depression.

5. The catheter system of claim 2 wherein the through port is disposed on a distal end of the depression.

6. The catheter system of claim 2 wherein the exit port passes through the protrusion.

7. The catheter system of claim 1 wherein the through port and the exit port comprise:
    guiding aids for the distal insertion of the guide wire.

* * * * *